US012788359B2

(12) United States Patent
Qun

(10) Patent No.: US 12,788,359 B2
(45) Date of Patent: Nov. 10, 2026

(54) PERSONAL SMART STETHOSCOPE AND AUSCULTATION METHOD USING COMPLEX BIO-SIGNAL SENSOR

(71) Applicants: INDUSTRY ACADEMIC COOPERATION FOUNDATION KEIMYUNG UNIVERSITY, Daegu (KR); CLAIRAUDIENCE CO., LTD., Daegu (KR)

(72) Inventor: Wei Qun, Daegu (KR)

(73) Assignees: INDUSTRY ACADEMIC COOPERATION FOUNDATION KEIMYUNG UNIVERSITY, Daegu (KR); CLAIRAUDIENCE CO., LTD., Daegu (KR)

( * ) Notice: Subject to any disclaimer, the term of this patent is extended or adjusted under 35 U.S.C. 154(b) by 271 days.

(21) Appl. No.: 18/723,788

(22) PCT Filed: Oct. 21, 2022

(86) PCT No.: PCT/KR2022/016160
§ 371 (c)(1),
(2) Date: Jun. 24, 2024

(87) PCT Pub. No.: WO2023/120925
PCT Pub. Date: Jun. 29, 2023

(65) Prior Publication Data

US 2025/0064422 A1 Feb. 27, 2025

(30) Foreign Application Priority Data

Dec. 24, 2021 (KR) ........................ 10-2021-0187624

(51) Int. Cl.
*A61B 7/04* (2006.01)
*A61B 5/024* (2006.01)
(Continued)

(52) U.S. Cl.
CPC ............ *A61B 7/04* (2013.01); *A61B 5/02411* (2013.01); *A61B 5/02416* (2013.01);
(Continued)

(58) Field of Classification Search
CPC .. A61B 7/04; A61B 7/00; A61B 7/003; A61B 5/28; A61B 5/00; A61B 5/0205;
(Continued)

(56) References Cited

U.S. PATENT DOCUMENTS 6,083,156 A * 7/2000 Lisiecki ............ A61B 5/02055 600/301
11,071,466 B2 7/2021 Huang et al.
(Continued)

FOREIGN PATENT DOCUMENTS

KR 10-0986022 B1 10/2010
KR 10-1436732 B1 9/2014
(Continued)

*Primary Examiner* — Chu Chuan Liu
(74) *Attorney, Agent, or Firm* — Bridgeway IP Law Group, PLLC; Sang Ho Lee; Hyun Woo Shin

(57) ABSTRACT

A smart stethoscope includes: a main body including a plurality of sensors for measuring a user's bio-signals and a power supply unit; and a fixing part coupled to a front side of the main body and provided to be foldable to fix a user's finger, wherein the main body includes: an input unit operated by a user; and a control unit that, when one of measurement modes is selected by the user's operation, measures a bio-signal at a specific sensor from among the plurality of sensors on the basis of the selected measurement mode, and calculates a measurement value corresponding to the measured bio-signal according to a preset algorithm. Accordingly, auscultation can be optimized for a user by changing a measurement frequency by changing the mode according to the user while allowing for auscultation
(Continued)

through multi-channels including electrocardiogram, pulse waves, and heart and lung sounds.

11 Claims, 7 Drawing Sheets

(51) Int. Cl.
*A61B 5/1455* (2006.01)
*A61B 5/28* (2021.01)
*A61B 7/00* (2006.01)

(52) U.S. Cl.
CPC ............ *A61B 5/14551* (2013.01); *A61B 5/28* (2021.01); *A61B 7/003* (2013.01)

(58) Field of Classification Search
CPC . A61B 5/024; A61B 5/02411; A61B 5/02416; A61B 5/1455; A61B 5/14551; A61B 5/14552; A61B 5/4362; A61B 5/6869
See application file for complete search history.

(56) References Cited

U.S. PATENT DOCUMENTS

| | | | | |
|---|---|---|---|---|
| 2017/0238812 | A1* | 8/2017 | Atlas .................... | A61B 5/0205 |
| 2019/0125187 | A1 | 5/2019 | Kuo et al. | |

FOREIGN PATENT DOCUMENTS

| | | | |
|---|---|---|---|
| KR | 10-2015-0081667 | A | 7/2015 |
| KR | 10-1616473 | B1 | 4/2016 |
| KR | 10-2018-0065039 | A | 6/2018 |
| KR | 20-0488626 | Y1 | 2/2019 |
| KR | 10-1957110 | B1 | 3/2019 |
| KR | 10-2020-0030496 | A | 3/2020 |
| KR | 10-2021-0135908 | A | 11/2021 |

* cited by examiner

PERSONAL SMART STETHOSCOPE AND AUSCULTATION METHOD USING COMPLEX BIO-SIGNAL SENSOR

TECHNICAL FIELD

The present invention relates to a personal smart stethoscope using a complex bio-signal sensor and an auscultation method, and more specifically, to a personal smart stethoscope using a complex bio-signal sensor, which can be worn on a part of a human body to measure a plurality of bio-signals, and an auscultation method.

BACKGROUND ART

Generally, stethoscopes are used to listen to arterial sounds, intestinal murmurs, and vascular sounds, as well as heart and breathing sounds, generating within a body, and to check whether the body is in a normal condition, and also to listen to brachial artery sounds when measuring blood pressure.

The current trend is to replace conventional analog stethoscopes with digital stethoscopes embedded with a microphone and a microcomputer, and the digital stethoscopes enable precise examination by analyzing stethoscope sounds or are used for educational purposes or the like.

However, since the conventional stethoscopes have a relatively simple function and may not provide multi-channel auscultation functions of auscultating electrocardiogram and pulse waves, in addition to heart and lung sounds. Further, they are structurally designed to be worn around the neck, and thus, they are inconvenient to use and keep.

In addition, the conventional general stethoscopes have an inconvenience of auscultating heart sounds of adults and infants while turning over both sides of the stethoscope head, and also have an economical problem since a general stethoscope for measuring heart sounds of pregnant women and a fetal stethoscope for measuring heart sounds of fetuses should be prepared separately.

In addition, Transcatheter Aortic Valve Implantation (TAVI), which is a representative treatment method for aortic valve stenosis, is a procedure of making a small incision in the femoral artery near the groin, inserting an artificial heart valve through the artery, and placing a tissue-type artificial heart valve in the area of the existing aortic valve narrowed by calcification. After the procedure, prognoses of the procedure are checked in a method such as echocardiography, magnetic resonance imaging, computed tomography, or the like. In this case, since there is a clear limitation in that it is difficult to confirm the prognoses in an external setting outside the hospital, there is a problem in that it is difficult for a patient who has undergone a procedure of transcatheter aortic valve implantation to confirm the prognoses in real time in daily lives. Although it is most effective to auscultate the heart sounds to confirm the prognoses of the procedure, since it is impossible for the general public, other than professional medical persons, to diagnose heart sound results, the need for a stethoscope that the general public may also use is emerging.

PRIOR ART DOCUMENTS

Patent Documents (Patent document 1) Korean Patent Registration No. 10-0986022

DISCLOSURE OF INVENTION

Technical Problem

Therefore, the present invention has been made in view of the above problems, and it is an object of the present invention to provide a personal smart stethoscope using a complex bio-signal sensor and an auscultation method, which can make auscultation optimized for a user by changing the mode and measurement frequency to be suitable for the user, while allowing auscultation of measuring electrocardiogram, pulse waves, and heart and lung sounds through multi-channels.

In addition, another object of the present invention is to provide a personal smart stethoscope using a complex bio-signal sensor and an auscultation method, which allow a user to immediately confirm measured values or transmit the measured values to an external device.

Technical Solution

To accomplish the above objects, according to one aspect of the present invention, there is provided a smart stethoscope comprising: a main body including a plurality of sensors for measuring bio-signals of a user and a power supply unit; and a fixing unit coupled on a front side of the main body in a foldable way to fix a user's finger, wherein the main body includes: an input unit handled by the user; and a control unit for measuring, when one of measurement modes is selected by handling of the user, a bio-signal through a specific sensor among the plurality of sensors on the basis of the selected measurement mode, and calculating a measurement value corresponding to the measured bio-signal according to a preset algorithm.

Here, the plurality of sensors may include: a heart sound sensor for measuring heart and lung sounds when a back side of the main body contacts a part of a human body; an electrocardiogram (ECG) sensor for measuring electrical activities of the heart when the back side of the main body contacts a part of the human body; a pulse wave (PPG: PhotoPlethysmoGraph) sensor for measuring changes of blood flow due to heartbeat when a user's finger is touched; and an oxygen saturation (SpO2, saturation of percutaneous oxygen) sensor for measuring concentration of oxygen in arterial blood when a user's finger is touched.

In addition, the measurement mode may include at least one among a pregnant woman mode, a heart mode, and a breathing mode.

In addition, when the selected measurement mode is the pregnant woman mode, the control unit may set a measurement frequency of the heart sound sensor to a heart sound frequency of a fetus, and measure a pulse wave of a mother, who is the user, through the pulse wave sensor, at the same time of measuring the heart sound frequency of a fetus through the heart sound sensor set to the heart sound frequency of a fetus.

In addition, when the selected measurement mode is the heart mode, the control unit may set a measurement frequency of the heart sound sensor to a general frequency, and measure an electrocardiogram and a pulse wave of the user through the electrocardiogram sensor and the pulse wave sensor, at the same time of measuring a heart sound frequency of the user through the heart sound sensor.

In addition, when the selected measurement mode is the breathing mode, the control unit may set a measurement frequency of the heart sound sensor to a lung sound frequency, and measure a heart sound frequency of the user through the heart sound sensor set to the lung sound frequency.

In addition, the main body may further include a communication unit; and an output unit located on a back side, wherein the control unit may control to output a pulse wave measured by the pulse wave sensor, oxygen saturation measured by the oxygen saturation sensor, and a type of measurement mode selected by the user through the output unit, and transmit a measurement value corresponding to the measured bio-signal to an external device according to a preset algorithm.

Meanwhile, the main body may further include: a groove which is a space that allows the fixing unit to be accommodated in the main body when the fixing unit is folded; and a contact groove located on the front side, where a part of the user's finger contacts while the finger is inserted in the fixing unit.

Here, the pulse wave sensor and the oxygen saturation sensor may be provided in the contact groove to be exposed to outside and in contact with the user's finger when the user's finger is fixed to the fixing unit.

In addition, the input unit may be located in the groove, and provided at a position facing a part of the fixing unit when the fixing unit is folded and accommodated in the groove.

In addition, the main body may be provided so that curvatures of the front side and the back side are different from each other and a height of a center point of the back side is greater than a height of the contact groove with respect to the ground when the back side faces the ground.

According to another aspect of the present invention, there is provided an auscultation method performed by a smart stethoscope, the method comprising the steps of: selecting one of measurement modes by handling of a user; setting a measurement criterion of a specific sensor among a plurality of sensors on the basis of the selected measurement mode; measuring a bio-signal of the user through a plurality of sensors; calculating a measurement value corresponding to the measured bio-signal according to a preset algorithm; outputting the calculated measurement value; and transmitting the calculated measurement value to an external device.

Here, the plurality of sensors may include: a heart sound sensor for measuring heart and lung sounds when contacting a part of a human body; an electrocardiogram (ECG) sensor for measuring electrical activities of the heart when contacting a part of the human body; a pulse wave (PPG) sensor for measuring changes of blood flow due to heartbeat; and an oxygen saturation ($SpO_2$) sensor for measuring concentration of oxygen in arterial blood.

In addition, the measurement mode may include at least one among a pregnant woman mode, a heart mode, and a breathing mode.

In addition, when the measurement mode selected at the step of selecting one of measurement modes is the pregnant woman mode, a measurement frequency of the heart sound sensor may be set to a heart sound frequency of a fetus at the step of setting a measurement criterion of a specific sensor among a plurality of sensors on the basis of the selected measurement mode, and a pulse wave of a mother, who is the user, may be measured through the pulse wave sensor, at the same time of measuring the heart sound frequency of a fetus through the heart sound sensor at the step of measuring a bio-signal.

In addition, when the measurement mode selected at the step of selecting one of measurement modes is the heart mode, a measurement frequency of the heart sound sensor may be set to a general frequency at the step of setting a measurement criterion of a specific sensor among a plurality of sensors on the basis of the selected measurement mode, and an electrocardiogram and a pulse wave of the user may be measured through the electrocardiogram sensor and the pulse wave sensor, at the same time of measuring a heart sound frequency of the user through the heart sound sensor at the step of measuring a bio-signal.

In addition, when the measurement mode selected at the step of selecting one of measurement modes is the breathing mode, a measurement frequency of the heart sound sensor may be set to a lung sound frequency at the step of setting a measurement criterion of a specific sensor among a plurality of sensors on the basis of the selected measurement mode, and a heart sound frequency of the user may be measured through the heart sound sensor at the step of measuring a bio-signal.

Advantageous Effects

According to an aspect of the present invention described above, as a personal smart stethoscope using a complex bio-signal sensor and an auscultation method are provided, it is possible to make auscultation optimized for a user by changing the mode and measurement frequency to be suitable for the user, while allowing auscultation of measuring electrocardiogram, pulse waves, and heart and lung sounds through multi-channels.

In addition, a user may immediately confirm measured values or transmit the measured values to an external device.

BEST MODE FOR CARRYING OUT THE INVENTION

Figure 1:
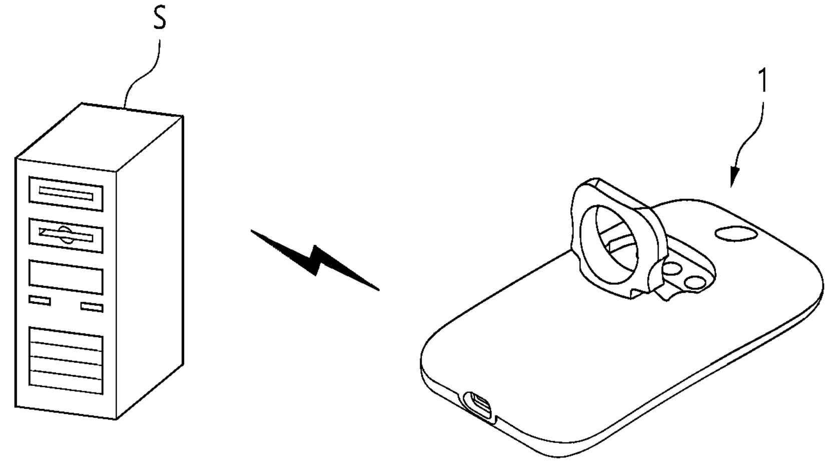
FIG. 1 is a view for explaining a system including a smart stethoscope of the present invention.

The detailed description of the present invention described below refers to the accompanying drawings, which show specific embodiments, in which the present invention may be embodied, as an example. These embodiments are described in detail as sufficient as to embody the present invention by those skilled in the art. It should be understood that although various embodiments of the present invention are different from each other, they do not need to be mutually exclusive. For example, specific shapes, structures, and characteristics described herein may be implemented in other embodiments without departing from the spirit and scope of the present invention in relation to an embodiment. In addition, it should be understood that the location or arrangement of individual components within each disclosed embodiment may be changed without departing from the spirit and scope of the present invention. Accordingly, the detailed description described below is not intended to be taken in a limiting sense, and the scope of the present invention is limited, if properly described, only by the appended claims, together with all the scopes equivalent to those claimed in the claims. In the drawings, similar reference numerals refer to identical or similar functions across several aspects.

Hereinafter, preferred embodiments of the present invention will be described in more detail with reference to the drawings.

Figure 8:
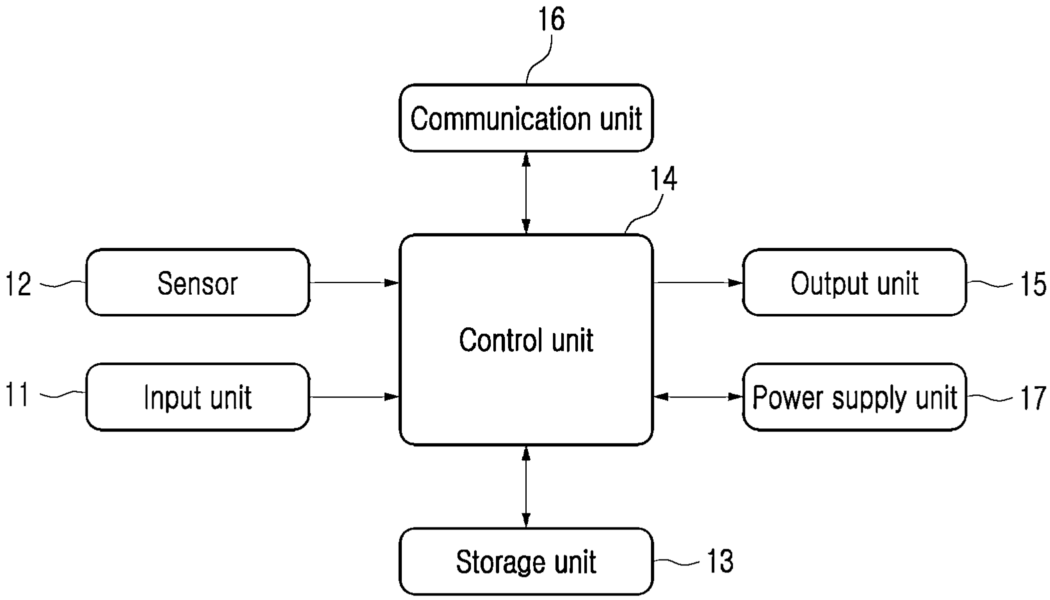
FIG. 8 is a block diagram for explaining the configuration of a smart stethoscope of the present invention.
Figure 9:
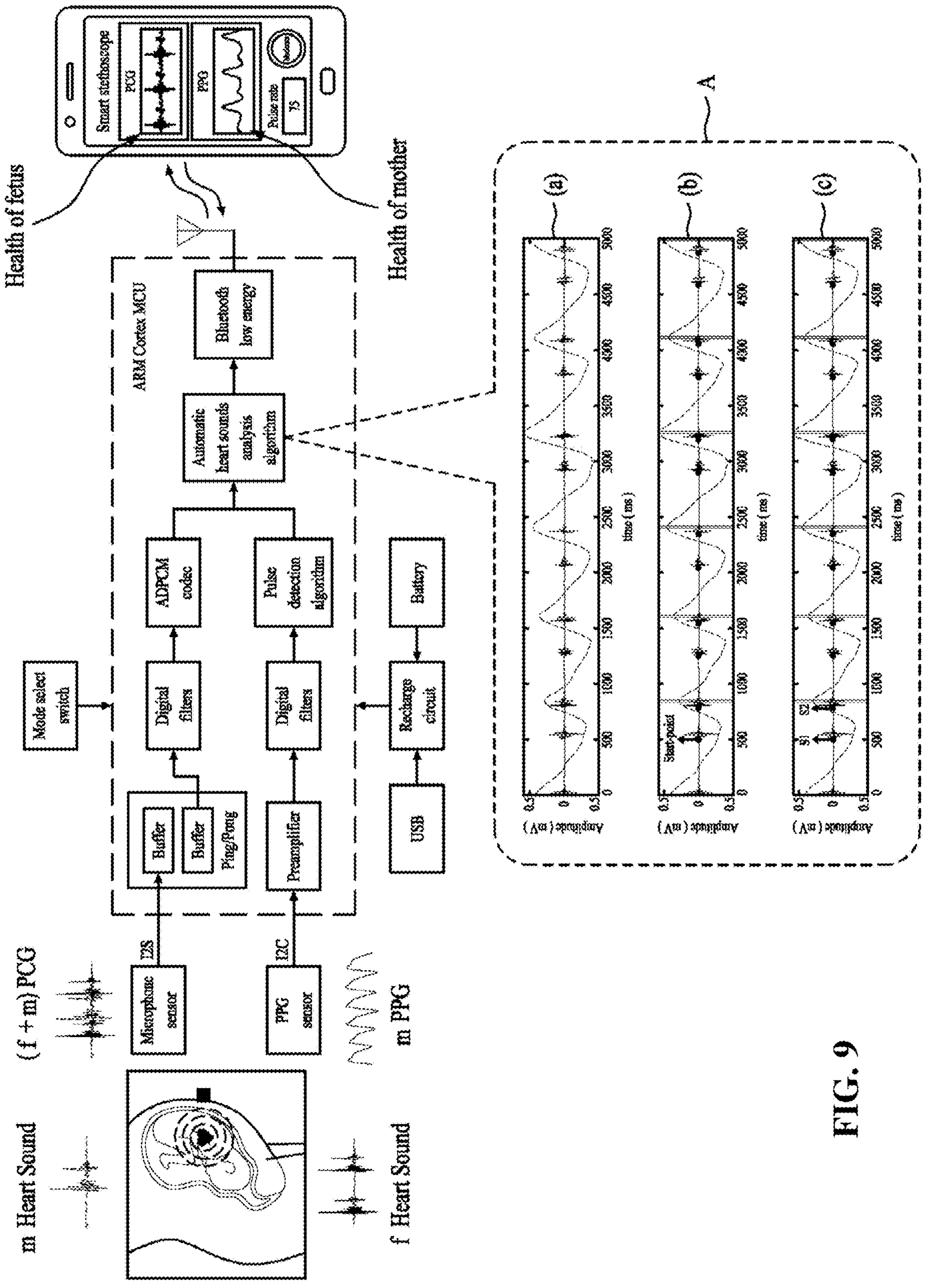
FIG. 9 is a schematic diagram showing measurement values output from an external device when the smart stethoscope of the present invention is in a pregnant woman mode.

FIG. 1 is a view for explaining a system including a smart stethoscope of the present invention, FIGS. 2 to 7 are views for explaining the external configuration of a smart stethoscope of the present invention, FIG. 8 is a block diagram for explaining the configuration of a smart stethoscope of the present invention, and FIG. 9 is a schematic diagram showing measurement values output from an external device when the smart stethoscope of the present invention is in a pregnant woman mode.

As shown in FIG. 1, a system including a smart stethoscope 1 according to this embodiment is configured to include an external device S and a smart stethoscope 1, and the external device S and the smart stethoscope 1 may be interconnected on the basis of network communication.

In addition, software for performing an auscultation method may be installed and executed in the external device S and the smart stethoscope 1 constituting the system of the present invention, and the configuration of the external device S and the smart stethoscope 1 may be controlled by the software for performing the auscultation method.

Although the external device S is shown as being provided as a server in FIG. 1, this is only an example for convenience of explanation, and it may be provided as a mobile terminal possessed by a user or a medical person, rather than a server. When the external device S is provided as a mobile terminal, it may transmit and receive information to and from the smart stethoscope 1 through short-distance communication or wired communication. Alternatively, when the external device S is provided as a server and a mobile terminal, the smart stethoscope 1 and the mobile terminal may transmit and receive information through the server.

The smart stethoscope 1 according to this embodiment is for making auscultation optimized for a user possible by changing the mode and measurement frequency to be suitable for the user, while allowing auscultation of measuring electrocardiogram, pulse waves, and heart and lung sounds through multi-channels, and may be provided to include a main body 10 and a fixing unit 20.

The main body 10 is provided to measure bio-signals from a user by contacting the user's body, and may include an input unit 11, a sensor 12, a storage unit 13, a control unit 14, an output unit 15, a communication unit 16, a power supply unit 17, a groove H1, a contact groove H3, and a charging port H5, and the input unit 11, the sensor 12, the output unit 15, the groove H1, and the contact groove H3 may be provided on the outer surface of the frame F, which is the exterior of the main body 10, to be exposed.

First, in the case of the frame F, which is the exterior of the main body 10, curvatures of the front and back sides are provided to be different from each other as shown in FIG. 1, and this is to improve the sense of grip when the user holds the main body 10 at the time of measuring bio-signals while a user's finger is inserted in the fixing unit 20.

More specifically, in using the stethoscope 1 according to this embodiment, the front side of the main body 10 is the surface that is in contact with the user's palm and fingers, and the back side of the main body 10 is the surface that is in contact with the user's torso such as the chest or abdomen, and as the body parts being in contact are different, the front and back sides of the main body 10 may be provided at a curvature suitable for each body part that is in contact.

Figure 5:
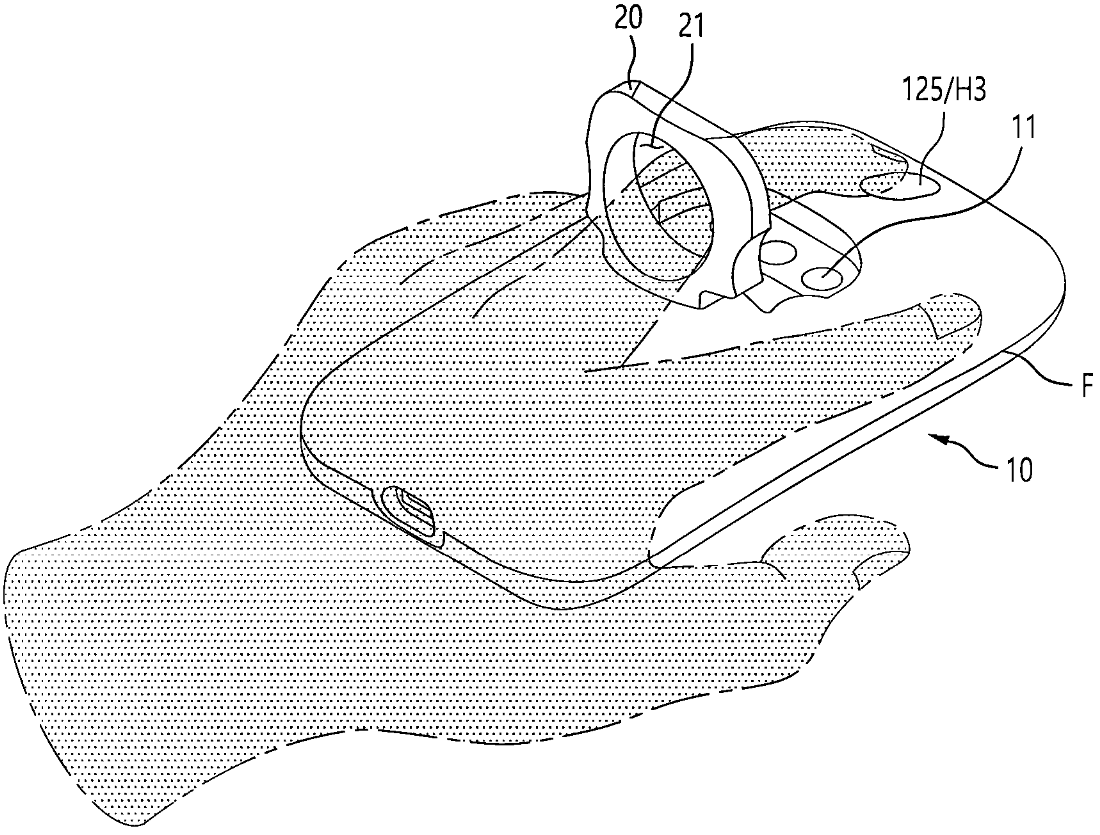
Figure 6:
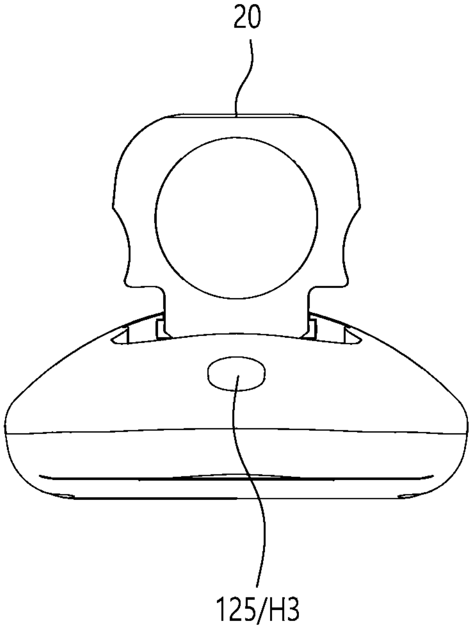
Figure 7:
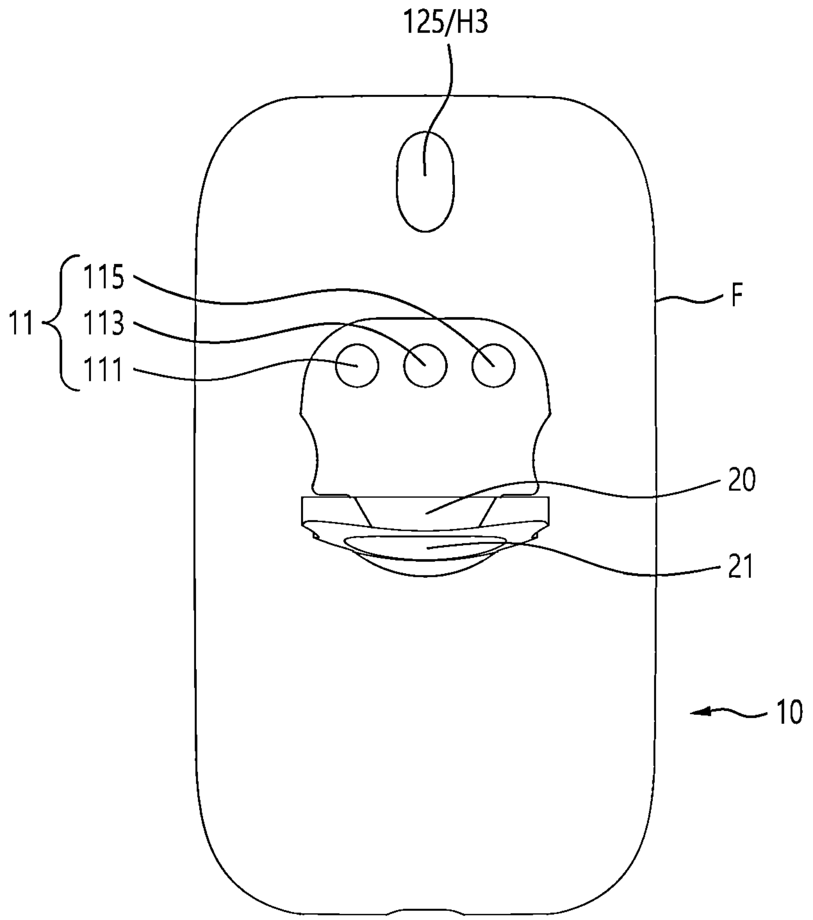

Particularly, when the back side of the main body 10 faces the ground as shown in FIG. 5, as the front side is provided so that the height of the center point of the back side is greater than the height of the contact groove H3 with respect to the ground, the front side of the main body 10 has a curvature larger than that of the back side of the main body 10, and the user may hold and fix the front side of the main body 10 in his hand more stably.

In addition, the main body 10 according to the present embodiment may be provided in a shape in which both side surfaces, which do not have the contact groove H3 and the charging port H5, are recessed toward the groove H1 at a predetermined curvature, and this may be intended to improve accuracy of collected bio-signals by minimizing contact of both side surfaces of the main body 10 with the human body while measuring the bio-signals.

Meanwhile, the input unit 11 constituting the main body 10 is a part exposed on the outer surface of the frame F to be handled by the user, and the input unit 11 may be provided inside the groove H1 at a position facing a part of the fixing unit 20 when the fixing unit 20 is folded and accommodated in the groove H1. In addition, the input unit 11 may be provided to include at least one among a pregnant woman mode button 111, a heart mode button 113, and a breathing mode button 115 as a button for changing the measurement mode.

The sensor 12 may be provided in plural to measure user's complex bio-signals, and the stethoscope 1 according to the present invention may include a heart sound sensor 121, an electrocardiogram sensor, a pulse wave sensor 125, and an oxygen saturation sensor 125 as a plurality of sensors 12.

First, the heart sound sensor 121 may be provided on the back side of the main body 10, i.e., on the back side of the frame F, to measure heart and lung sounds when the back side of the main body 10 contacts a part of the human body. More specifically, the heart sound sensor 121 is a type of sound sensor that can measure sounds including the sounds generated by the apex (end of the heart) and the base of the heart generated when the heart contracts and expands.

Particularly, the heart sound sensor 121 of the present invention may be configured of two types of sensors including a heart and lung sound sensor (not shown) for measuring heart sounds and a noise detection sensor (not shown) for measuring noise.

The heart and lung sound sensor (not shown) may be installed on the outer surface of the back side of the main body 10 direct contacting the user's body, and the noise detection sensor (not shown) may be installed at a location that does not directly contact the user's body. Through this, the heart and lung sound sensor (not shown) may measure heart sounds much better, and the noise detection sensor (not shown) may precisely measure even the noise generated by other organs, in addition to the heart, which is the target of examination, or flow of blood or water, as well as the noise external to the human body.

More specifically, for example, the smart stethoscope 1 of the present invention may eliminate noise included in the heart and lung sounds by removing signals corresponding to at least part of the signal measured by the noise detection sensor (not shown) from the signal measured by the heart and lung sound sensor (not shown) through the control unit 14 described below. That is, in a method of removing noise signals from signal-processed heart sounds, noise measured together at the time of measuring the heart sounds can be eliminated, and only pure heart sounds can be provided.

The electrocardiogram (ECG) sensor 123 is provided in the main body 10 to measure electrical activities of the heart when the back side of the main body 10 contacts a part of the human body. To this end, the electrocardiogram sensor 123 may be installed on the back side of the main body 10 to be exposed, but it may also be embedded in the back side of the main body 10 as shallow as a minimum depth to maximize the contact with the surface of the user's body.

The electrocardiogram sensor 123 includes a first electrode 1231 and a second electrode 1235, and the electrocardiogram may be measured by the first electrode 1231 and the second electrode 1235 having opposite polarities.

Figure 2:
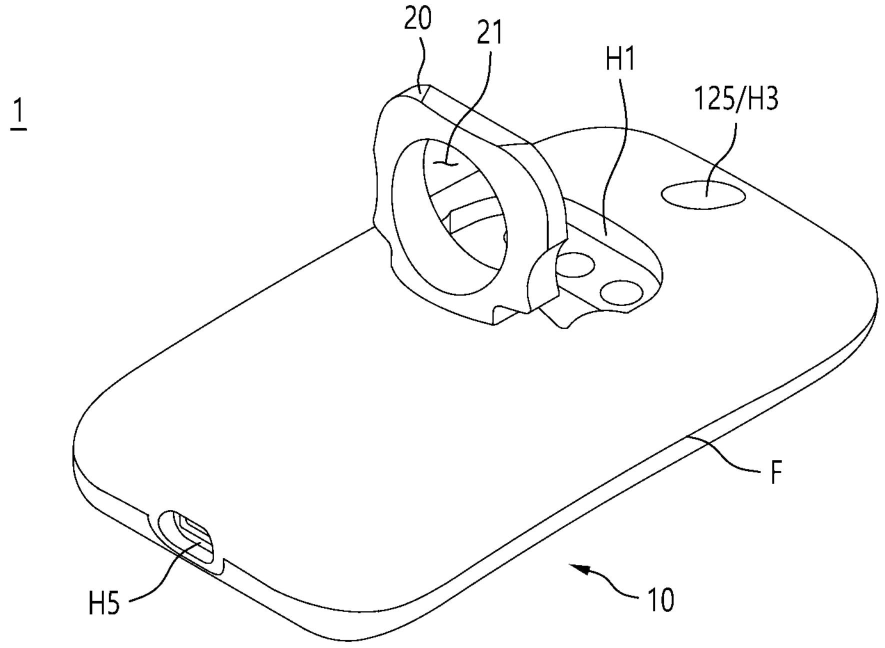
FIGS. 2 to 7 are views for explaining the external configuration of a smart stethoscope of the present invention.
Figure 3:
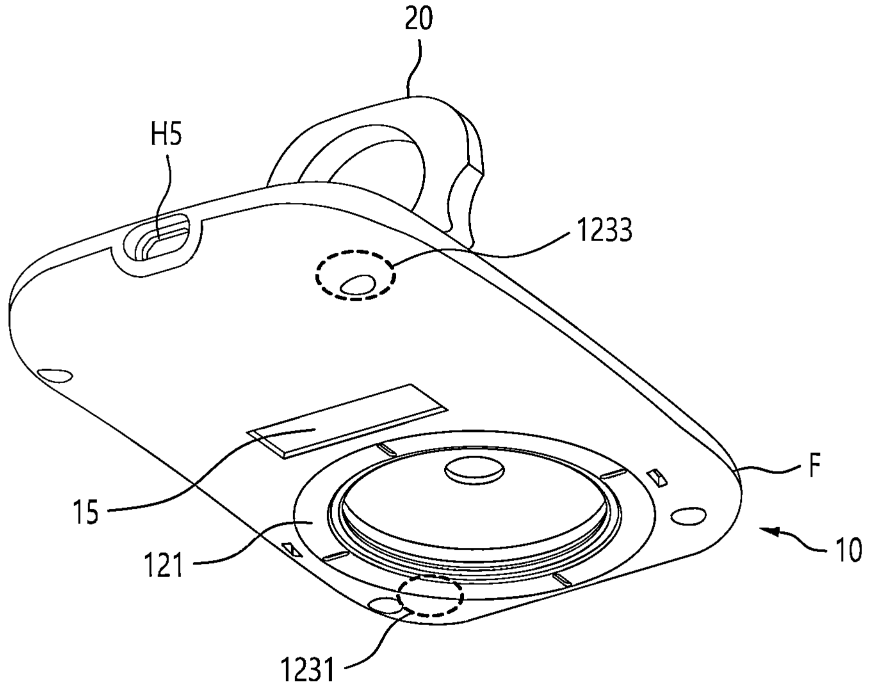
Figure 4:
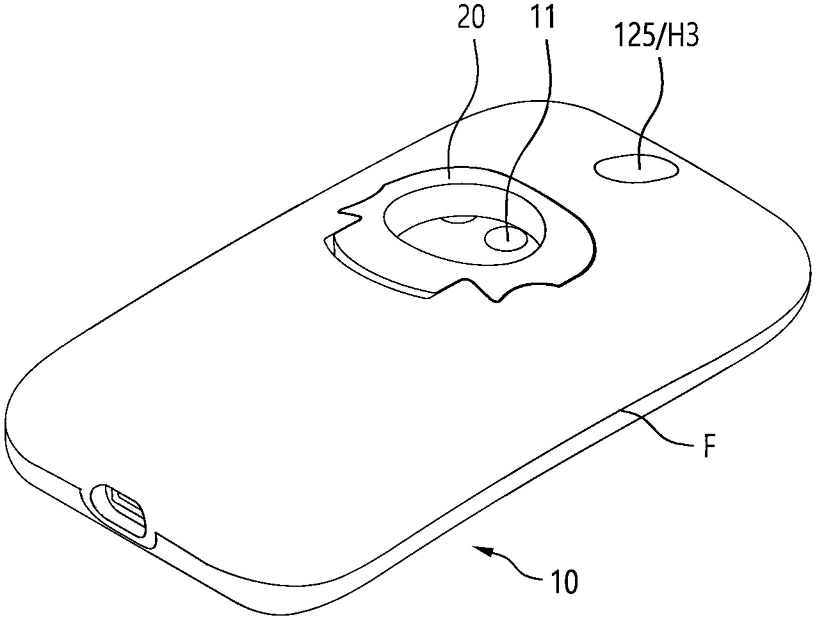

In addition, the first electrode 1231 and the second electrode 1235 of the electrocardiogram sensor 123 may be provided at the locations that can facilitate the contact with the human body. Specifically, when the first and second electrodes are placed on the back side of the main body 10, which is provided to have a predetermined curvature, to face the ground, they may be positioned at the lowest places on the back side with respect to the ground as shown in FIG. 2.

Meanwhile, the pulse wave (PPG: PhotoPlethysmoGraph) sensor 125 is provided to measure changes of blood flow due to heartbeat, i.e., the pulse waves, and it is provided in the contact groove H3 provided on the front side of the main body 10 to measure changes of blood flow due to heartbeat when a user's finger is inserted in the fixing unit 20 and a part of the finger inserted into the fixing unit 20 is touched.

In addition, the pulse wave sensor 125 may use a reflective pulse wave (PPG: PhotoPlethysmoGraph) sensor of a method that measures a signal reflected and returned after a light source penetrates into the skin.

For example, as the pulse wave sensor 125 is configured to include a light emitting source and a light receiver, when light emitted from the light source is radiated onto the human body, the light is absorbed in the blood, bones, and tissues, and some of the light is reflected and received by the light receiver. The amount of the absorbed light is proportional to the amount of skin, tissue, and blood in the path through which the light passes, and as the amount of the absorbed light does not change, except the change of blood flow due to heartbeat, change of blood flow may be measured using the reflected light.

Meanwhile, the oxygen saturation (SpO2, saturation of percutaneous oxygen) sensor 125 is provided to measure concentration of oxygen in the arterial blood, and the oxygen saturation sensor 125 may be provided in the contact groove H3 of the main body 10. The oxygen saturation sensor 125 may be a sensor integrated with the pulse wave sensor 125 described above. That is, it may be configured as a multi-function sensor that may measure both the pulse wave and oxygen saturation using one sensor.

Accordingly, the smart stethoscope 1 according to this embodiment may simultaneously measure the pulse wave and oxygen saturation when the tip of a finger contacts the contact groove H3 while a user inserts the finger into the fixing unit 20.

The storage unit 13 corresponds to a data storage memory and may store bio-signals detected by the sensor 12 starting from the time point of beginning supply of power to the smart stethoscope 1 by the power supply unit 17. In addition, the storage unit 13 may store identification information for identifying an external device for transmitting the measurement values calculated by the control unit 14 to the external device through the communication unit 16. In addition, the storage unit 13 may store software (application) for performing the auscultation method, and stores an algorithm for processing information generated by the communication unit 16 and the control unit 14 and the bio-signals.

The control unit 14 may control each component according to the software (application) for performing the auscultation method installed in the storage unit 13, and calculate measurement values corresponding to the bio-signals by changing the measurement mode on the basis of information that is input from the input unit 11 and processing the bio-signals measured by at least one sensor among the plurality of sensors 12 on the basis of the changed measurement mode according to a preset algorithm. Here, the measurement mode may be one among the pregnant woman mode, the heart mode, and the breathing mode.

In addition, the control unit 14 may analyze the characteristics of the noise included in the heart and lung sounds and remove the noise included in the heart sound by analyzing any one or more among the frequency, waveform pattern, and magnitude of the noise signal according to a preset algorithm.

In addition, when the measurement mode selected by the user is the pregnant woman mode, as shown in FIG. 9, the control unit 14 may set the measurement frequency of the heart sound sensor 121 to the heart sound frequency of a fetus, and measure the pulse wave (PPG) of a mother, i.e., a pregnant woman, who is the user, through the pulse wave sensor 125, at the same time of measuring the heart sound frequency of a fetus f through the heart sound sensor 121.

More specifically, in the case of a pregnant woman, when the heart sound of an unborn baby is the subject of examination, the heart sound m of the mother, who is a pregnant woman, is also considered as a noise. In this case, as shown in FIG. 9, only the heart sound f of the baby may be provided by removing the mother's heart sound m detected together with the heart sound f of the baby according to an algorithm A for identifying and separating previously stored fetal heart sounds.

In addition, when the heart sound frequency f of a fetus is measured, the pregnant woman's pulse wave (PPG) may be used to remove the mother's heart sound m, and the pregnant woman's pulse wave (PPG) and heart rate may also be observed.

Therefore, when the measurement mode is the pregnant woman mode, health of both the fetus and the pregnant woman can be monitored.

To this end, the smart stethoscope 1 of the present invention may measure continuous heart sounds through a ping/pong buffer as shown in FIG. 9 and may implement multi-task through FreeRTOS.

In addition, when the selected measurement mode is the heart mode, the control unit 14 may set the measurement frequency of the heart sound sensor 121 to a general frequency, and measure the electrocardiogram and pulse waves of the user through the electrocardiogram sensor 123 and the pulse wave sensor 125, at the same time of measuring the heart sound frequency of the user through the heart sound sensor 121.

In addition, when the selected measurement mode is the breathing mode, the control unit 14 may set the measurement frequency of the heart sound sensor 121 to a lung sound frequency, and measure the heart sound frequency of the user through the heart sound sensor 121.

The control unit 14 may remove some of the bio-signals collected based on the measurement mode or collect and process only specific bio-signals, and transfer the measurement value, which is a processed result, to the output unit 15 to be output through the output unit 15, or transmit the measurement value to an external device through the communication unit 16.

More specifically, for example, when the measurement mode is the pregnant woman mode, as shown in FIG. 9, the heart sound of the fetus, obtained by removing the heart sound of the pregnant woman from the frequency of combining the heart sounds of the fetus and the pregnant woman through a specific algorithm A, and the measured pulse waves of the mother may be output through an external device and provided to the user. At this point, an application for providing the user with the measurement value, which a result of processing by the smart stethoscope 1, may be stored in the external device.

Therefore, the control unit 14 may confirm the measured pulses, oxygen saturation, battery state, and measurement mode, as well as the result calculated from the measured bio-signals, through the output unit 15.

In addition, although not shown in the drawing, the smart stethoscope 1 may further include a separate switch for turning power on and off in the input unit 11 or the frame F.

Meanwhile, the output unit 15 may be provided at a position adjacent to the heart sound sensor 121 on the back side of the main body 10 as shown in FIG. 2 to output the measurement value calculated by the control unit 14. The output unit 15 is a display device, and although the output unit 15 is assumed to be provided as an OLED display in the present invention, it is not limited thereto.

More specifically, the output unit 15 may be provided to include a Digital to Analog Converter (DAC) and a 3.5 mm earphone connection terminal so that the calculated measured value may be provided to the user as auditory information although there is no external device such as a smartphone.

The communication unit 16 may be provided to transmit the measurement value calculated by the control unit 14 to an external device S possessed or designated by the user. In addition, the communication unit 16 may transmit and receive various information for performing the auscultation method through an external network.

The power supply unit 17 is provided to supply power to the sensor 12, the control unit 14, the output unit 15, and the communication unit 16, which are components constituting the smart stethoscope 1 of the present invention, and may include a battery, and it can be connected to the charging port H5 for charging the battery.

In addition, the groove H1 is a space provided at a part on the front side of the frame F forming the exterior of the main body 10 to accommodate the fixing unit 20 when the smart stethoscope 1 is not in use. A plurality of buttons 111, 113, and 115 constituting the input unit 11 may be placed inside the groove H1.

Meanwhile, the contact groove H3 is provided on the front side of the main body 10, i.e., on the front side of the frame F, at a position where a part of a user's finger contacts while the user's finger is inserted in the fixing unit 20. As the pulse wave sensor 125 and the oxygen saturation sensor 125 are provided on the surface of the contact groove H3, the smart stethoscope 1 of the present invention may measure the pulse wave and oxygen saturation only by inserting the user's finger into the fixing unit 20. To this end, the longitudinal central axis of the contact groove H3 may be provided to be positioned on the same line as the longitudinal central axis of the groove H1.

Meanwhile, the charging port H5 is provided on one side of the main body 10, more preferably, on a side surface that is symmetrical to the side surface adjacent to the contact groove H3 as shown in the drawings to charge the battery included in the power supply unit 17. The charging port H5 may also be used as a communication port for data transmission, in addition to charging the battery.

Meanwhile, the fixing unit 20 is coupled on the front side of the main body 10 in a foldable way to fix a user's finger, and to this end, it may include a hole 21 into which the finger may be inserted. In addition, as a part of the fixing unit 20 is folded through a hinge member (not shown) while being coupled to the groove H1 of the main body 10, the fixing unit 20 may be inserted and stored inside the groove H1 when the smart stethoscope 1 according to this embodiment is not in use.

Meanwhile, the smart stethoscope 1 according to another embodiment of the present invention may provide the first electrode 1231 and the second electrode 1235 constituting the electrocardiogram sensor 123 at the positions symmetrical to each other with respect to an imaginary center line, such as the top and bottom surfaces, on the inner peripheral surface of the hole 21 of the fixing unit 20 to be used as an electrocardiogram sensor 123, rather than providing the first electrode 1231 and the second electrode 1235 on the back side of the main body 10.

In addition, the fixing unit 20 may be used as a switch for turning on and off the smart stethoscope 1 as another embodiment. More specifically, an input unit 11 including a plurality of buttons 111, 113, and 115 is provided inside the groove H1 as an electrostatic or pressure sensor. Accordingly, when the smart stethoscope 1 is not in use, the off state is maintained as the fixing unit 20 is accommodated inside the groove H1 and in contact with the input unit 11, and when the fixing unit 20 is taken out of the groove H1 and the contact with the input unit 11 is released, it may turn to the on state. To this end, the fixing unit 20 may be made of a conductive material to electrically transfer signals to the input unit 11, or may be provided to be in contact with the input unit 11 when the fixing unit 20 is folded and accommodated to have a rotation angle that may apply pressure to the input unit 11 and maintain the state of contacting the input unit 11 when it is accommodated. To this end, a protrusion member (not shown) may be further included to prevent the fixing unit 20 from being arbitrarily separated from the groove H1 by an external pressure unintended by the user when once a part of the fixing unit 20 is accommodated in the groove H1. This protrusion member (not shown) may be a member provided on the inner peripheral surface of the groove H1 to press the fixing unit 20.

Figure 10:
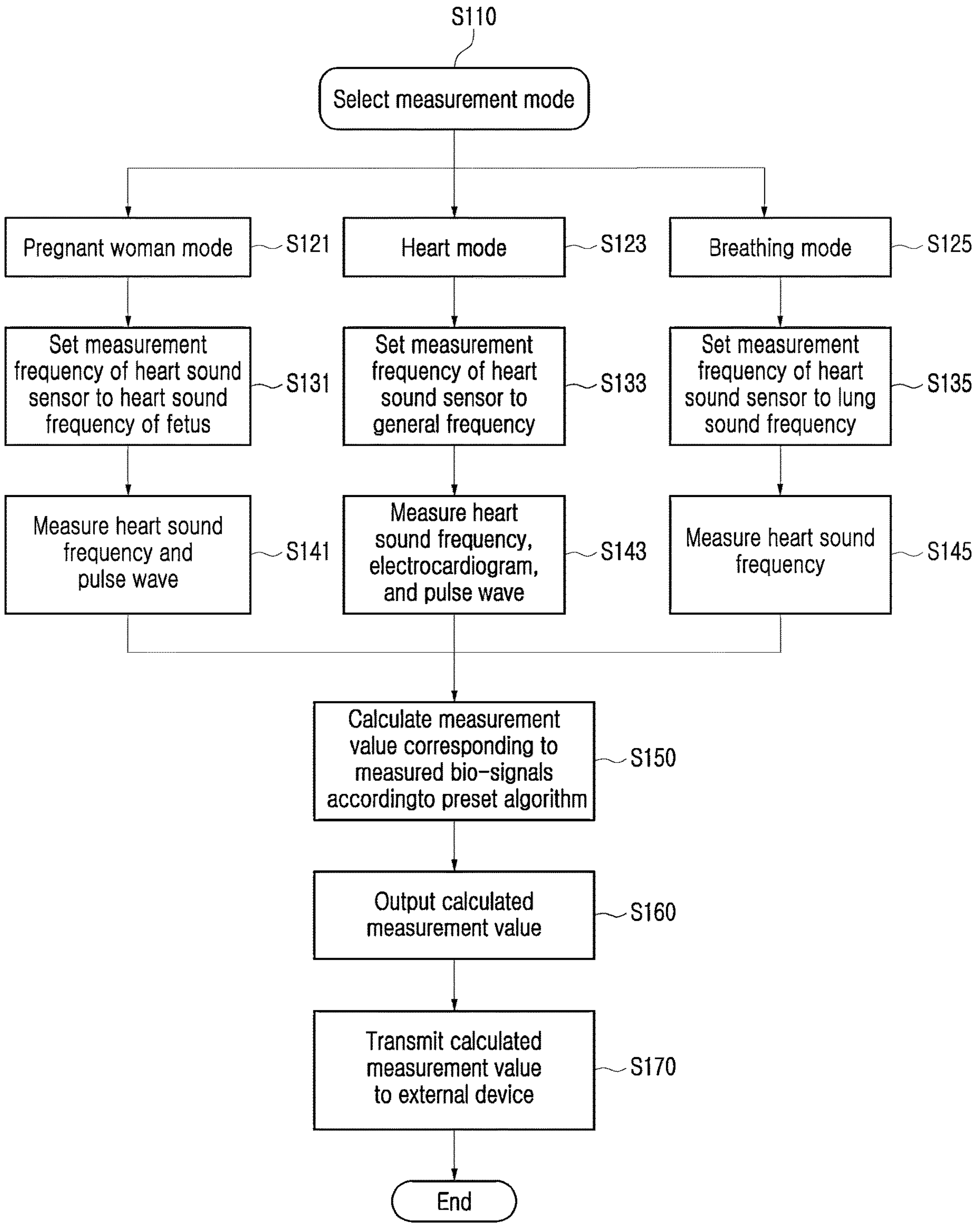
FIG. 10 is a flowchart illustrating an auscultation method according to an embodiment of the present invention.

Meanwhile, FIG. 10 is a flowchart illustrating an auscultation method according to an embodiment of the present invention, and the auscultation method of the present invention is performed by installing software (application) for performing the auscultation method in the smart stethoscope 1 described above. Hereinafter, content that overlaps with the smart stethoscope 1 described above or content that can be inferred will be omitted.

First, the smart stethoscope 1 may perform a step of selecting one of the measurement modes by handling of a user (S110). At the step of selecting a measurement mode (S110), the user may select the measurement mode by handling at least one among a pregnant woman mode button 111, a heart mode button 113, and a breathing mode button 115 constituting the input unit 11.

In addition, the smart stethoscope 1 may perform a step of setting a measurement criterion of a specific sensor (S131, S133, or S135) among a plurality of sensors on the basis of the selected measurement mode (S121, S123, or S125). At the step of setting a measurement criterion of a specific sensor (S131, S133, S135), when the selected measurement mode is the pregnant woman mode (S121) as shown in the drawing, the measurement frequency of the heart sound sensor 121 may be set to the heart sound frequency of a fetus (S131).

At the step of setting a measurement criterion of a specific sensor (S131, S133, S135), when the selected measurement mode is the heart mode (S123) as shown in the drawing, the measurement frequency of the heart sound sensor 121 may be set to a general frequency (S133).

In addition, at the step of setting a measurement criterion of a specific sensor (S131, S133, S135), when the selected measurement mode is the breathing mode (S125) as shown in the drawing, the measurement frequency of the heart sound sensor 121 may be set to the lung sound frequency (S135).

Thereafter, the smart stethoscope 1 may perform a step of measuring bio-signals of a user through a plurality of sensors (S141, S143, or S145). At the step of measuring bio-signals (S141, S143, or S145), when the selected measurement mode is the pregnant woman mode (S121), the pulse wave of a mother, i.e., a pregnant woman, who is the user, may be measured through the pulse wave sensor 125, at the same time of measuring the heart sound frequency of a fetus through the heart sound sensor 121 (S141).

Then, at the step of measuring bio-signals (S141, S143, or S145), when the selected measurement mode is the heart mode (S123), the electrocardiogram and pulse waves of the user are measured through the electrocardiogram sensor 123 and the pulse wave sensor 125, at the same time of measuring the heart sound frequency of the user through the heart sound sensor 121 (S143).

In addition, at the step of measuring bio-signals (S141, S143, or S145), when the selected measurement mode is the breathing mode (S125), the heart sound frequency of the user may be measured through the heart sound sensor 121 (S145).

In addition, at the step of measuring bio-signals (S141, S143, or S145), the bio-signals may be collected continuously for at least 20 seconds in measuring a plurality of bio-signals.

Meanwhile, at the step of measuring bio-signals (S141, S143, or S145), when measurement of the bio-signals is completed based on the measurement mode for a predetermined period of time, a step of calculating a measurement value corresponding to the measured bio-signals may be performed according to a preset algorithm (S150). The preset algorithm may be an algorithm previously stored in the storage unit 13 or may be received by the user through the communication unit 16.

Then, the smart stethoscope 1 may output the measurement value calculated from the bio-signals through the output unit 15 provided on the back side of the main body 10 by performing a step of outputting the calculated measurement value (S160).

Thereafter, the smart stethoscope 1 may perform a step of transmitting the calculated measurement value to an external device S (S170). The step of transmitting to an external device S is transmitting the measurement value to a mobile terminal such as a smartphone possessed by the user, and the measurement value may be transmitted through wireless communication such as Bluetooth through the communication unit 16, and the measurement value may also be transmitted through wired communication using the charging port H5. Of course, it is not limited thereto, and as described above, when the external device S is provided as a server, it may also be transmitted to the mobile terminal indirectly through the server.

Components according to the present invention are components defined not by physical classification but by functional classification, and may be defined by the functions performed by each component. Each component may be implemented as hardware or program codes and processing units that perform respective functions, and functions of two or more components may be implemented to be included in one component. Therefore, the names given to the components in the following embodiments are not to physically distinguish each component, but to imply a representative function performed by each component, and it should be noted that the technical spirit of the present invention is not limited by the names of the components.

The auscultation method of the present invention as described above may be implemented in the form of program instructions that can be executed through various computer components and recorded in a computer-readable recording medium. The computer-readable recording medium may store program instructions, data files, data structures, and the like alone or in combination.

The program instructions recorded in the computer-readable recording medium may be specially designed and configured for the present invention or may be known to and used by those skilled in the field of computer software.

Examples of the computer-readable recording medium include magnetic media such as hard disks, floppy disks, and magnetic tapes, optical media such as CD-ROMs and DVDs, magneto-optical media such as floptical disks, and hardware devices specially configured to store and execute program instructions, such as ROM, RAM, flash memory, and the like.

Examples of the program instructions include high-level language codes that can be executed by a computer using an interpreter, as well as machine language codes such as those produced by a compiler. The hardware devices described above may be configured to operate as one or more software modules to perform the processes according to the present invention, and vice versa.

Although various embodiments of the present invention have been shown and described above, the present invention is not limited to the specific embodiments described above, and of course, various modified embodiments are possible by those skilled in the art without departing from the gist of the present invention claimed in the claims, and these modified embodiments should not be individually understood from the technical spirit or prospect of the present invention.

| DESCRIPTION OF SYMBOLS |
| --- |
| 1: Smart stethoscope |
| 10: Main body |
| 11: Input unit |
| 12: Sensor |
| 13: Storage unit |
| 14: Control unit |
| 15: Output unit |
| 16: Communication unit |
| 17: Power supply unit |
| F: Frame |
| H1: Groove |
| H3: Contact groove |
| H5: Charging port |
| 20: Fixing unit |
| 21: Hole |

The invention claimed is:

1. A smart stethoscope comprising:

a main body including a plurality of sensors configured to measure one or more bio-signals of a user and a power supply unit; and a foldable fixing member coupled to one side of the main body and including a hole configured to accommodate a finger of the user inserted therein, wherein the main body comprises:

an input interface configured to be operated by the user;

a control processor for measuring, when one of measurement modes is selected by operation of the user, a bio-signal through a specific sensor among the plurality of sensors based on the selected measurement mode, and calculating a measurement value corresponding to the measured bio-signal according to a preset algorithm;

a groove disposed on the one side of the main body and configured to accommodate the foldable fixing member in the main body when the foldable fixing member is in a folded state; and a contact groove disposed on the one side of the main body and configured to contact a part of the finger of the user when the finger is fixed to the foldable fixing member, and wherein the plurality of sensors comprises:

a heart sound sensor configured to measure heart and lung sounds when another side of the main body is configured to contact a part of a human body;

an electrocardiogram (ECG) sensor configured to measure electrical activities of a heart when the another side of the main body is configured to contact the part of the human body;

a pulse wave (PPG: PhotoPlethysmoGraph) sensor configured to measure changes of blood flow due to heartbeat when configured to be in contact with the finger of the user; and an oxygen saturation (SpO2, saturation of percutaneous oxygen) sensor configured to measure concentration of oxygen in arterial blood when configured to be in contact with the finger of the user.

2. The stethoscope of claim 1, wherein the measurement mode comprises at least one among a pregnant woman mode, a heart mode, and a breathing mode.

3. The stethoscope according to claim 2, wherein when the selected measurement mode is the pregnant woman mode, the control processor sets a measurement frequency of the heart sound sensor to a heart sound frequency of a fetus, and the control processor is configured to measure a pulse wave of a mother, who is the user, through the pulse wave sensor, concurrently with the heart sound frequency of the fetus through the heart sound sensor.

4. The stethoscope of claim 2, wherein when the selected measurement mode is the heart mode, the control processor sets a measurement frequency of the heart sound sensor to a general frequency, and the control processor is configured to measure an electrocardiogram and a pulse wave of the user through the electrocardiogram sensor and the pulse wave sensor, concurrently with a heart sound frequency of the user through the heart sound sensor.

5. The stethoscope of claim 2, wherein when the selected measurement mode is the breathing mode, the control processor sets a measurement frequency of the heart sound sensor to a lung sound frequency, and is configured to measure a heart sound frequency of the user through the heart sound sensor set to the lung sound frequency.

6. The stethoscope of claim 2, wherein the main body further comprises:

a communication unit; and an output unit disposed on the another side of the main body, wherein the control processor is configured to control the output unit to output a pulse wave measured by the pulse wave sensor, oxygen saturation measured by the oxygen saturation sensor, and a type of measurement mode selected by the user through, and to transmit the measurement value corresponding to the measured bio-signal to an external device according to the preset algorithm.

7. The stethoscope of claim 1, wherein the pulse wave sensor and the oxygen saturation sensor are disposed in the contact groove, are exposed to an outside, and are configured to be in contact with the finger of the user when the finger is fixed to the foldable fixing member.

8. The stethoscope of claim 7, wherein the input interface is disposed in the groove at a position facing a part of the foldable fixing member when the foldable fixing member is in the folded state and is accommodated in the groove.

9. The stethoscope according to claim 1, wherein a curvature of the one side of the main body and a curvature of the another side of the main body are different from each other, and a height of a center point of the main body is greater than a height of the contact groove with respect to a ground when the another side faces the ground.

10. An auscultation method performed by a smart stethoscope, the method comprising:

selecting one of measurement modes by operation of a user;

setting a measurement criterion of a specific sensor among a plurality of sensors based on the selected measurement mode;

measuring a bio-signal of the user through the plurality of sensors;

calculating a measurement value corresponding to the measured bio-signal according to a preset algorithm;

outputting the calculated measurement value; and transmitting the calculated measurement value to an external device, wherein the plurality of sensors comprises:

a heart sound sensor configured to measure heart and lung sounds when configured to contact a part of a human body;

an electrocardiogram (ECG) sensor configured to measure electrical activities of a heart when configured to contact the part of the human body;

a pulse wave (PPG) sensor configured to measure changes of blood flow due to heartbeat; and an oxygen saturation (SpO2) sensor configured to concentration of oxygen in arterial blood, wherein the measurement modes comprises a pregnant woman mode, and wherein when the selected measurement mode is the pregnant woman mode, a measurement frequency of the heart sound sensor is set to a heart sound frequency of a fetus at a step of setting the measurement criterion of the specific sensor among the plurality of sensors, and a pulse wave of a mother, who is the user, is measured through the pulse wave sensor, concurrently with the heart sound frequency of a fetus through the heart sound sensor at the step of measuring the bio-signal.

11. An auscultation method performed by a smart stethoscope, the method comprising:

selecting one of measurement modes by operation of a user;

setting a measurement criterion of a specific sensor among a plurality of sensors based on the selected measurement mode;

measuring a bio-signal of the user through the plurality of sensors;

calculating a measurement value corresponding to the measured bio-signal according to a preset algorithm;

outputting the calculated measurement value; and transmitting the calculated measurement value to an external device, wherein the plurality of sensors comprises:

a heart sound sensor configured to measure heart and lung sounds when configured to contact a part of a human body;

an electrocardiogram (ECG) sensor configured to measure electrical activities of a heart when configured to contact the part of the human body;

a pulse wave (PPG) sensor configured to measure changes of blood flow due to heartbeat; and an oxygen saturation (SpO2) sensor configured to concentration of oxygen in arterial blood, wherein the measurement mode comprises at least one among a heart mode, and a breathing mode, and wherein when the selected measurement mode is the heart mode, a measurement frequency of the heart sound sensor is set to a general frequency at a step of setting the measurement criterion of the specific sensor among the plurality of sensors, and an electrocardiogram and a pulse wave of the user are measured through the electrocardiogram sensor and the pulse wave sensor, concurrently with a heart sound frequency of the user through the heart sound sensor at the step of measuring the bio-signal, and wherein when the selected measurement mode is the breathing mode, the measurement frequency of the heart sound sensor is set to a lung sound frequency at the step of setting the measurement criterion of the specific sensor among the plurality of sensors, and the heart sound frequency of the user is measured through the heart sound sensor at the step of measuring the bio-signal.

* * * * *